(12) United States Patent
Reina et al.

(10) Patent No.: US 11,134,905 B2
(45) Date of Patent: Oct. 5, 2021

(54) X-RAY IMAGE DETECTOR HOLDER AND MOUNTING DEVICE AND METHOD FOR COMMERCIAL X-RAY APPLICATIONS

(71) Applicants: Leo Reina, Cary, IL (US); Steven A. Gdula, Crystal Lake, IL (US); James Sorgani, Cary, IL (US)

(72) Inventors: Leo Reina, Cary, IL (US); Steven A. Gdula, Crystal Lake, IL (US); James Sorgani, Cary, IL (US)

(73) Assignee: X-Ray Cassette Repair Co, Inc., Crystal Lake, IL (US)

( * ) Notice: Subject to any disclaimer, the term of this patent is extended or adjusted under 35 U.S.C. 154(b) by 85 days.

(21) Appl. No.: 16/672,454

(22) Filed: Nov. 2, 2019

(65) Prior Publication Data

US 2020/0155089 A1   May 21, 2020

Related U.S. Application Data

(60) Provisional application No. 62/755,091, filed on Nov. 2, 2018.

(51) Int. Cl.
*G21K 1/02* (2006.01)
*A61B 6/00* (2006.01)

(52) U.S. Cl.
CPC .......... *A61B 6/4291* (2013.01); *A61B 6/4411* (2013.01); *A61B 6/4283* (2013.01)

(58) Field of Classification Search
CPC .... A61B 6/06; A61B 6/08; A61B 6/40; A61B 6/4283; A61B 6/4291; G21K 1/025; G21K 1/04; G21K 1/06
See application file for complete search history.

(56) References Cited

U.S. PATENT DOCUMENTS

2005/0175154 A1\* 8/2005 Kondradsson ........... A61B 6/06
378/155
2006/0222149 A1\* 10/2006 O'Dea ................... G03B 42/04
378/186

\* cited by examiner

*Primary Examiner* — Don K Wong
(74) *Attorney, Agent, or Firm* — Clifford H. Kraft

(57) ABSTRACT

A device for attaching an x-ray grid holder to a commercial structure such as a pipe so that the modern digital grid can be used in analysis and inspection. The x-ray grid holder attach device is constructed to be attached to a structure and can include a flat grid holder part, the grid holder part having at least one peripheral slot; a structure contact part constructed to be strapped to a structure to be x-rayed, the structure contact part having a key sized to mate with the peripheral slot, the key having a lock constructed to hold the key in the peripheral slot; the structure contact part can a means to attach it to the structure to be x-rayed such as a strap or suction cups.

21 Claims, 10 Drawing Sheets

Prior Art

X-RAY IMAGE DETECTOR HOLDER AND MOUNTING DEVICE AND METHOD FOR COMMERCIAL X-RAY APPLICATIONS

This application is related to and claims priority to U.S. Provisional Patent application No. 62/755,091 filed Nov. 2, 2018. Application 62/755,091 is hereby incorporated by reference in its entirety.

FIELD OF THE INVENTION

The present invention relates generally to commercial x-ray applications and more particularly to an x-ray grid panel holder mounting device and method that allows a wide range of x-ray grids to be used in commercial applications.

DESCRIPTION OF THE PROBLEM SOLVED

X-ray has been used commercially to detect defects in commercial structures including pipelines, bridges and buildings. These applications are often conducted under demanding conditions not experienced in typical medical x-ray applications. X-ray grids are sensitive and, in the case of digital radiographic panels, expensive. Such commercial applications include an x-ray generator and an x-ray grid panel that can be of various types, placed in a panel holder or encasement designed to provide rigidity and protection for the grid during the x-ray operation. The panel holder function is to hold the x-ray grid on the surface of the object to allow a capture of the x-ray image. Devices that capture x-ray images range from photographic film to modern digital photosensitive devices. The grid holder holds the sensitive photo-device or surface flat and secure and allows handling. However, x-ray grids are nevertheless very sensitive to shock, heat and rough handling. Unfortunately, shock, heat and rough handling is very common in commercial applications such as x-raying a pipe or building structure. In particular, the very expensive x-ray grids are usually destroyed and rendered useless if dropped, bent or exposed to excessive heat.

Prior art techniques for holding an x-ray grid against an object usually consists of tying the grid in place with straps or the like. This has many disadvantages. First, the grid is a flat plate-like element, and the pipe or structure is cylindrical or has some other non-flat surface shape. This many times can cause the grid to not lie orthogonal to the x-ray beam, to shift position after being secured or to be bent by excessive strapping force. Second, such makeshift securing of the grid leads to grids being subjected to damaging stresses, or to fall loose or other movement that destroys the grid. Moreover, when the panel is placed on a hot surface the sensitive electronics in the panel can be damaged or render imperfect images of the subject being x-rayed.

It would be tremendously advantageous to have a device and method to secure an x-ray grid to a commercial structure such as a pipe so that it is easy to mount, remains orthogonal to the beam, is securely held in position, safe from shifting or becoming loose and falling, and is held in a position above the object to prevent damage from over heating

SUMMARY OF THE INVENTION

The present invention relates to a device for attaching an x-ray grid holder to a commercial structure such as a pipe or other metal surface so that the digital grid can be safely and securely held in position for accurate analysis and inspection. The x-ray grid holder device is constructed in such a manner to allow it to be attached to a structure and can include a flat grid holder part, the grid holder part having at least one peripheral slot, a structure contact part constructed to be strapped or magnetically attached to the structure to be x-rayed, the structure contact part having a key sized to mate with the peripheral slot in the grid holder, the key having a lock constructed to hold the key in the peripheral slot, the structure contact part having a means to attach it to the structure to be x-rayed such that the grid, and grid encasement holder are positioned above the surface being x-rayed.

DESCRIPTION OF THE FIGURES

Attention is now directed to several drawings that illustrate features of the present invention.

Several figures and illustrations have been provided to aid in understanding the present invention. The scope of the present invention is not limited to what is shown in the figures.

DESCRIPTION OF THE PREFERRED EMBODIMENTS

The present invention relates to a device and method of securing an x-ray grid panel holder to a pipe or other structure.

Figure 1A:
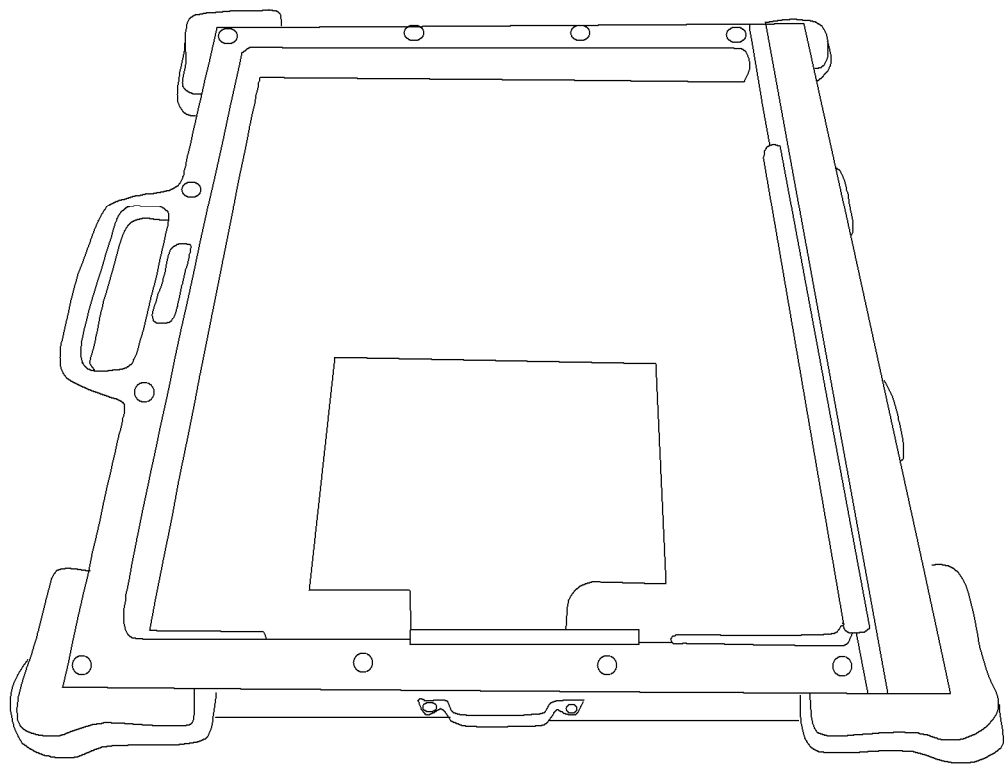
FIG. 1A is a prior art x-ray grid holder.

FIG. 1A shows a prior art x-ray panel holder. It can clearly be seen to be a delicate plate-like device with glass or other fragile material covering the photosensitive surface. Straps or cords loop through or attach to the metal handles for securing the device.

Figure 1B:
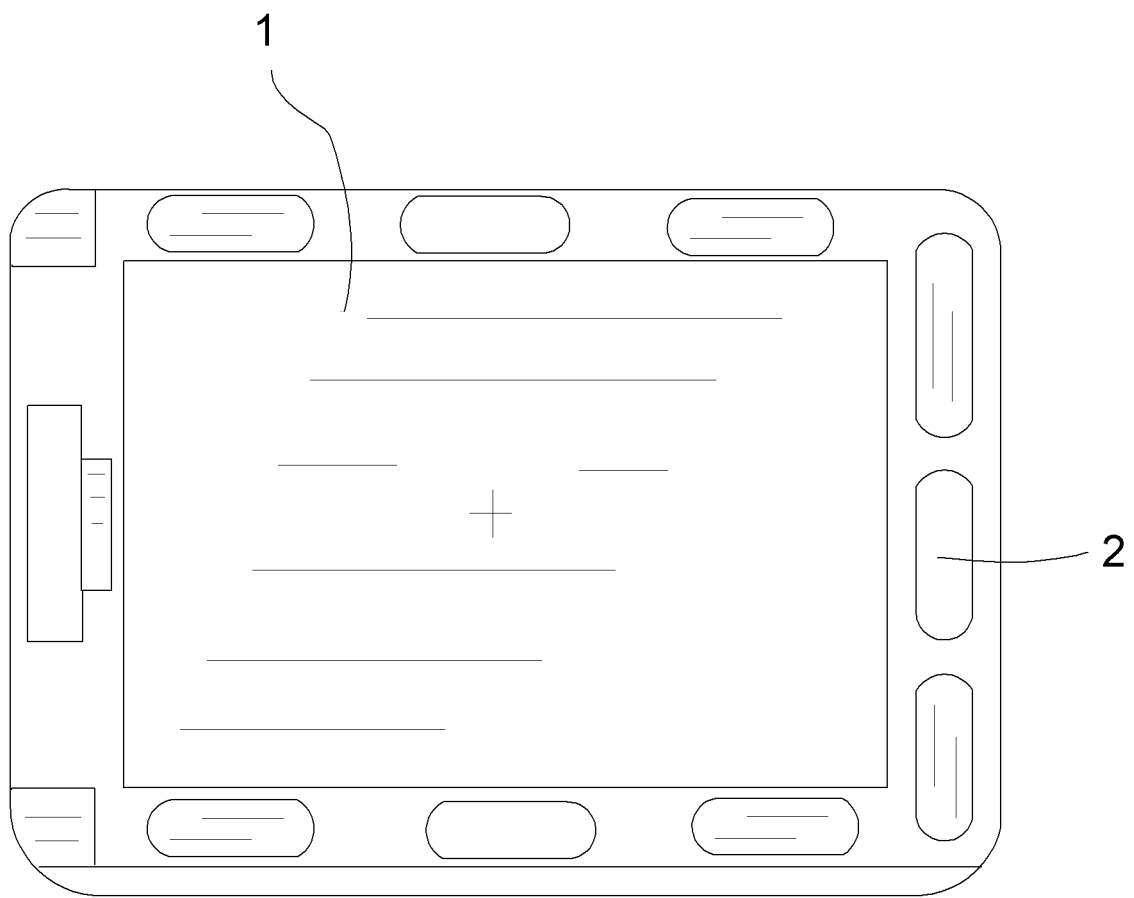
FIG. 1B is an embodiment of the grid holder part of the present invention.

A particular embodiment of the present invention secures the x-ray grid holder to a pipe; larger sized holders can be used to affix the grid holder to larger diameter pipes. Other embodiments can secure the grid holder to any shaped structure having either metallic and non metallic surfaces. The particular embodiment includes three parts: a grid panel holder, a grid holder part to secure the grid holder and a pipe strap part. FIG. 1B shows an embodiment of the grid holder part of the present invention. The central part 1 holds the x-ray grid, while the periphery includes handles with slots 2. The slots 2 are constructed and shaped to engage the pipe strap part.

Figure 2:
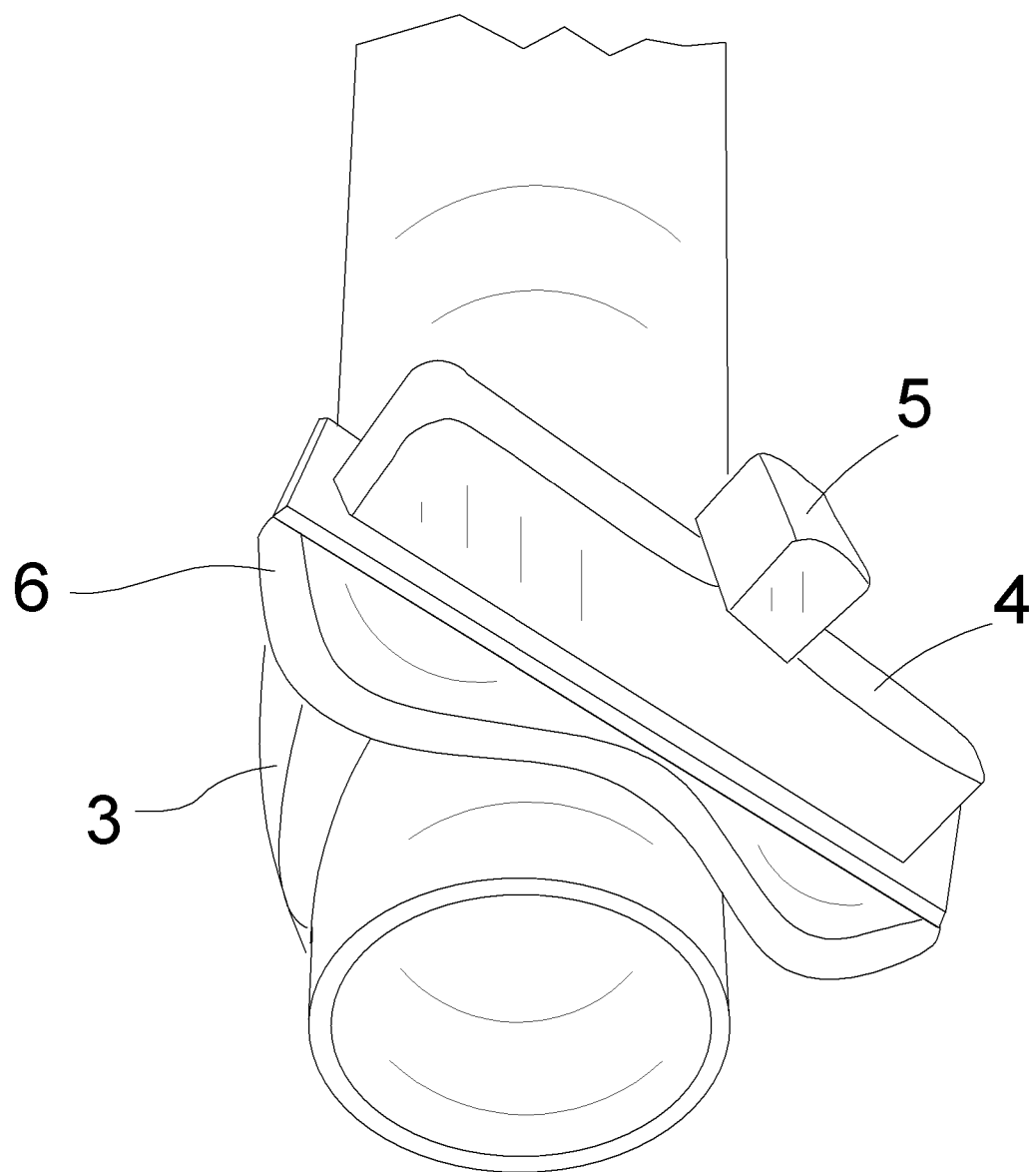
FIG. 2 is an embodiment of a pipe strap holder part of the present invention.

FIG. 2 shows an embodiment of the pipe strap part. A central section 6 is constructed to prevent the panel from contacting the surface of the pipe, which in some applications may be hot or cold. Contact of the panel holder with a hot surface can distort the image and/or damage the sensing devices in the x-ray cassette detector panel. This pipe strap part can be manufactured in different sizes to accommodate different ranges of pipe diameters. It can also be configured to affix to flat surfaces and held in place with magnets or suction cup. A key 4 matches the slot 2 in the grid holder part. A lock 5 secures the key 4 in the slot 2. A strap 3 secures the entire device to a pipe.

Figure 3:
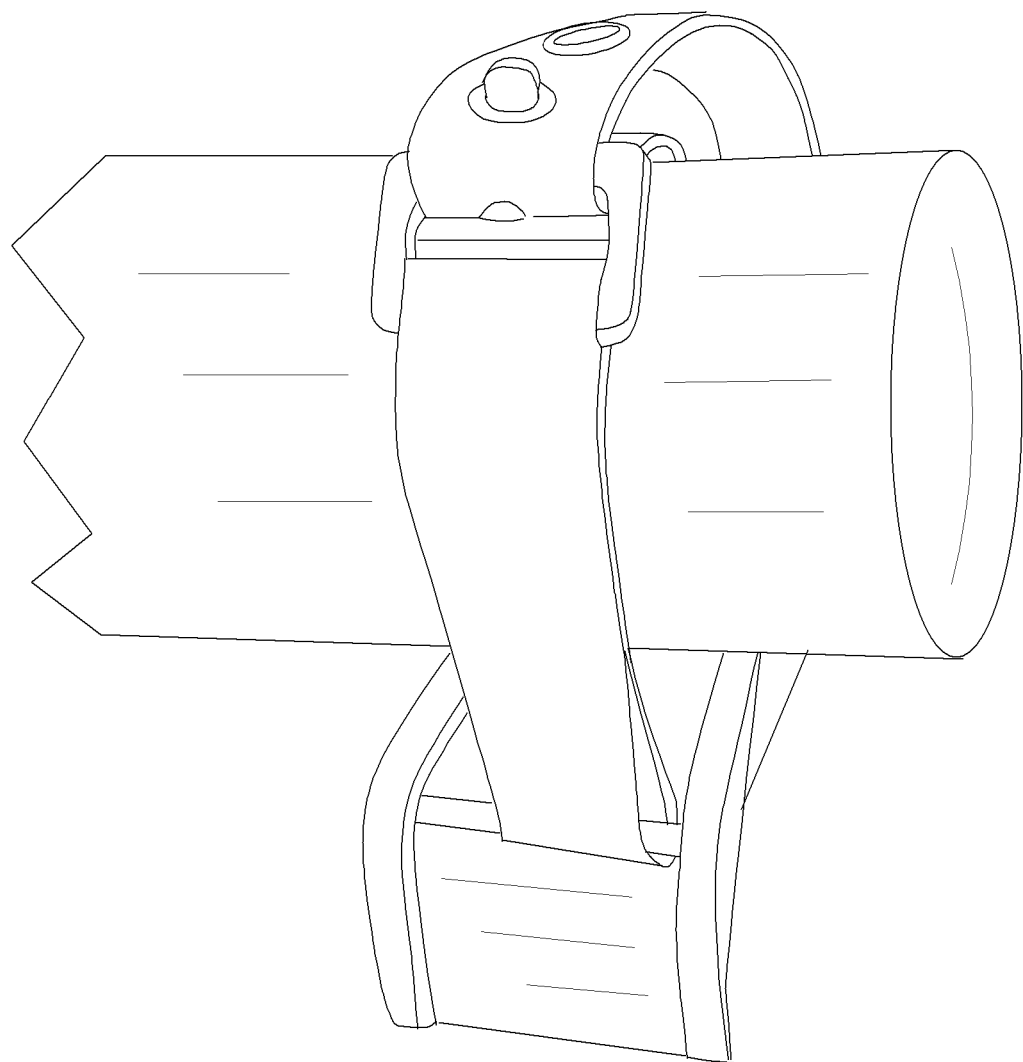
FIG. 3 shows the pipe strap part of FIG. 2 strapped to a pipe.
Figure 4:
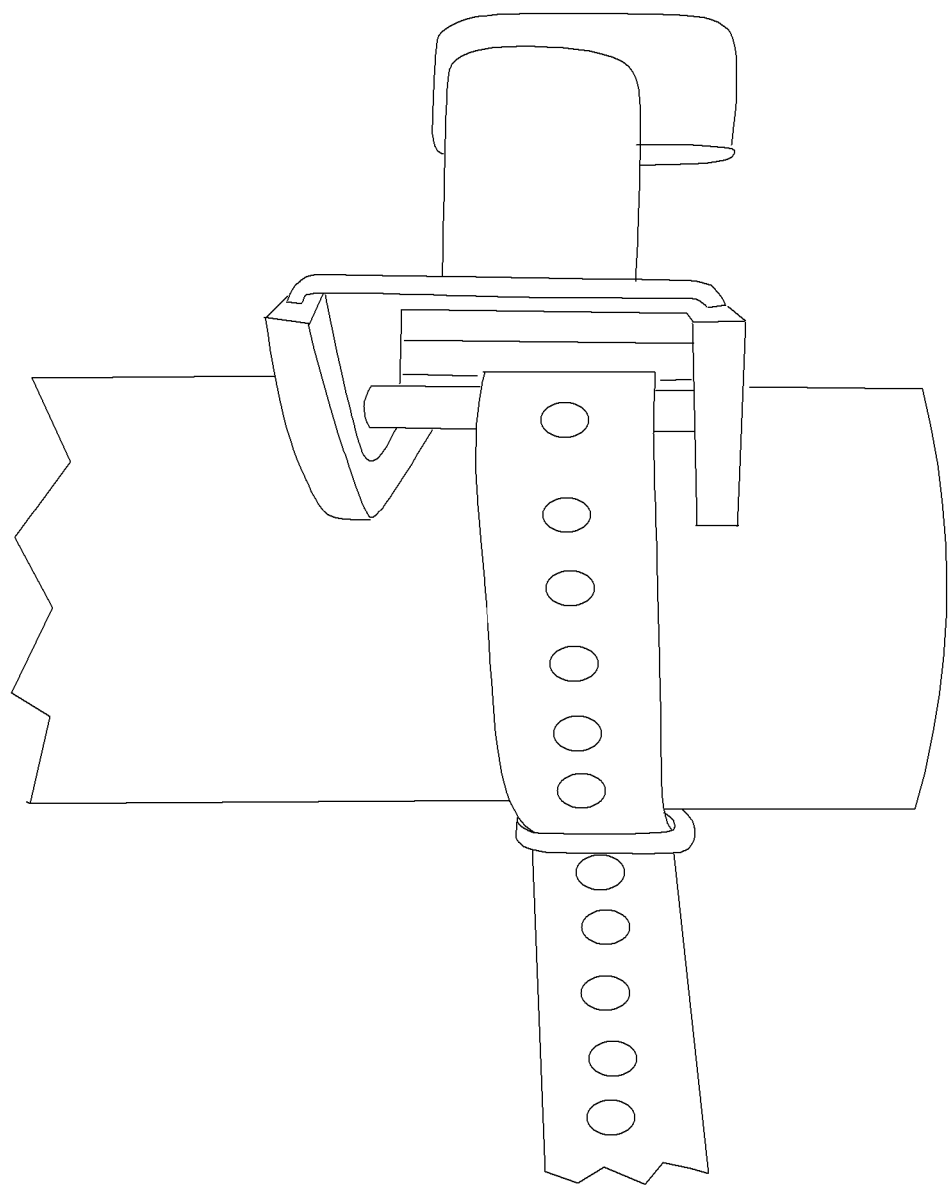
FIG. 4 is a different view of the part shown in FIG. 3.
Figure 5:
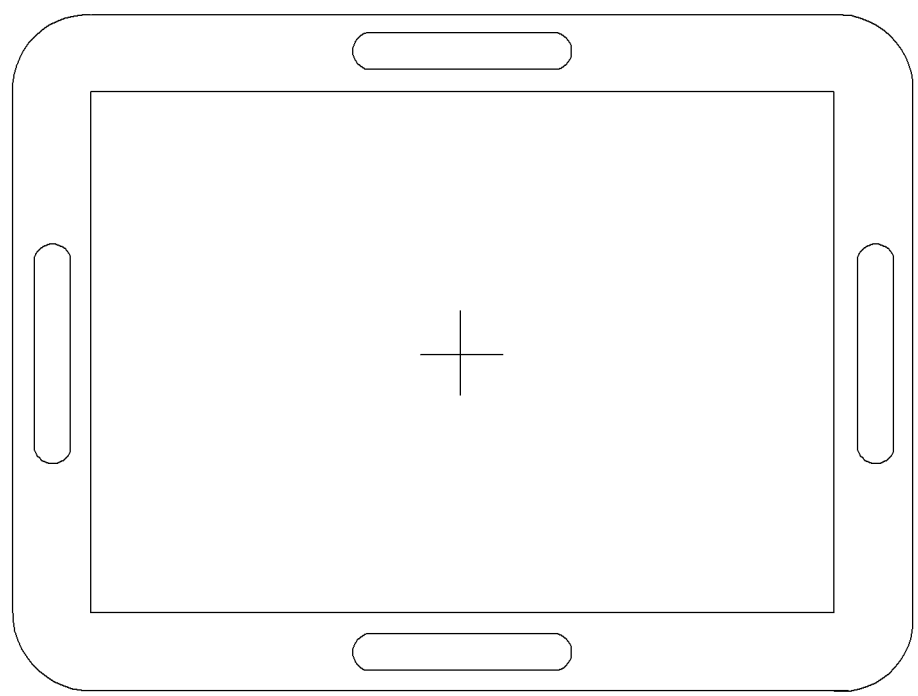
FIG. 5 is a different view of the grid holder part shown in FIG. 1B.

FIGS. 3-4 show different views of the pipe strap part secured to a pipe. FIG. 5 shows a different view of the grid holder part.

Figure 6:
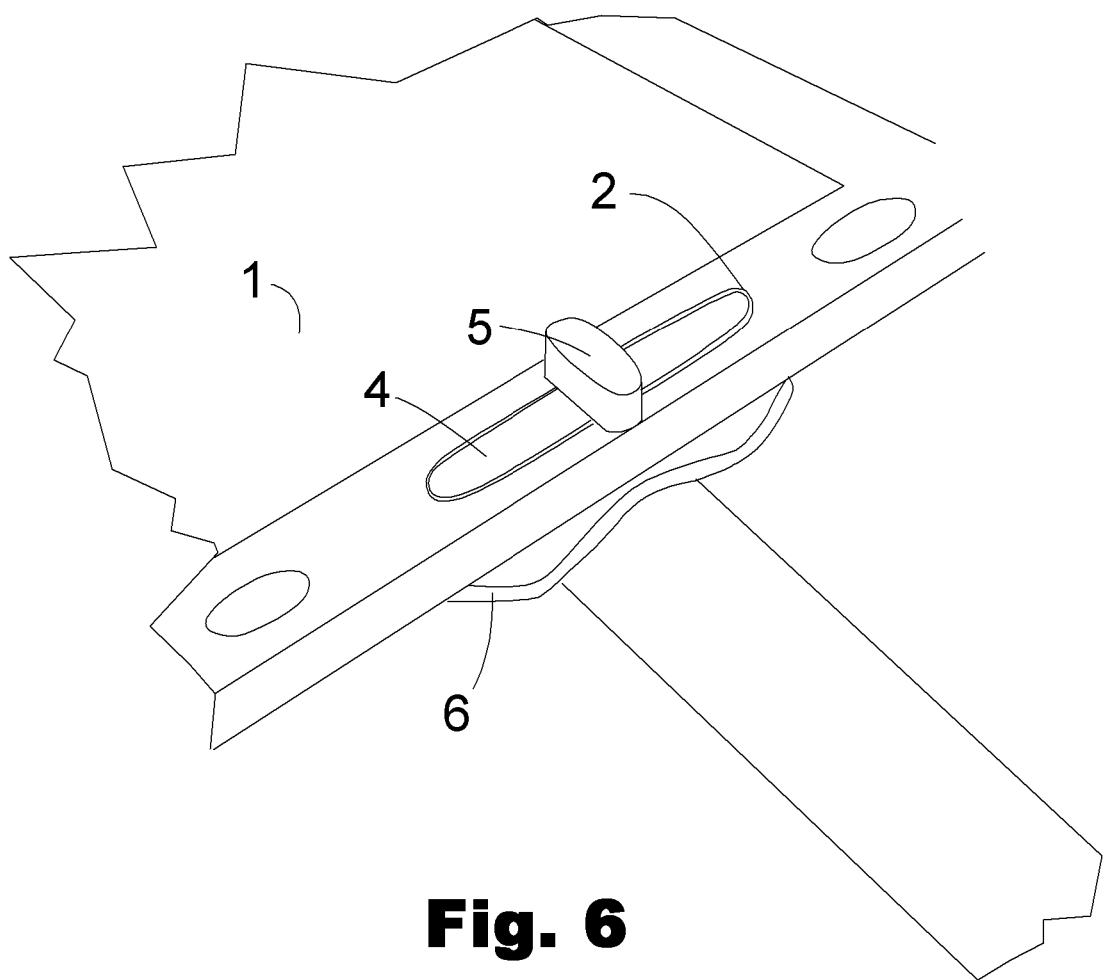
FIG. 6 shows the pipe strap part mated with the grid holder part.

FIG. 6 shows the entire device assembled and strapped to a pipe. The flat central part of the grid holder frame 1 holds the x-ray grid. The protruding key 4 slips into the elongated slot 2 and is secured by the somewhat elongated lock 5. The strap 3 holds the device in position on the pipe. The lock 5 can be turned to lock and hold the device to the x-ray grid holder frame 1 by providing a bias that pulls the protruding key 4 against the grid holder frame 1.

The device and parts of the present invention can be made from any rigid material with firm plastic being preferred. The strap can be an fiber strap that includes a buckle, VELCRO® or other attachment device. The grid holder part can attach in a similar way to other older parts designed for other types of structures besides pipes. In particular, a flat strap part can fit a beam or other flat or rectangular structure.

Figure 7:
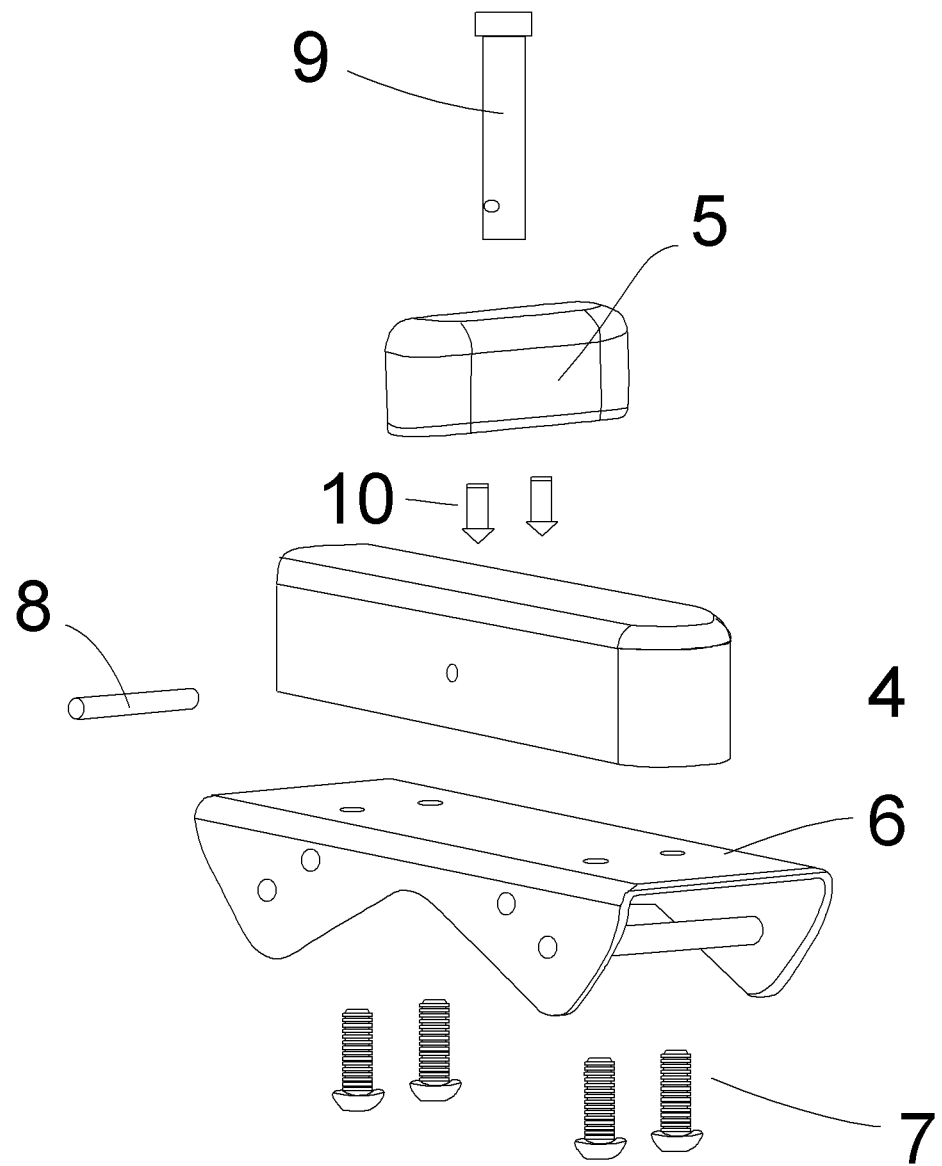
FIG. 7 shows an exploded view of the parts making up an embodiment of the present invention.

FIG. 7 shows an exploded view of the parts making up an embodiment of the present invention. A bracket 6 attached to a key 4. Two pins 10 hold the lock 5 to the key 4. An insertion pin 8 can also be used. A center axle 9 extends through the lock 5 into the key 4 and allows the lock 5 to turn. Four bolts 7 attach the key 4 to the bracket 6.

Figure 8:
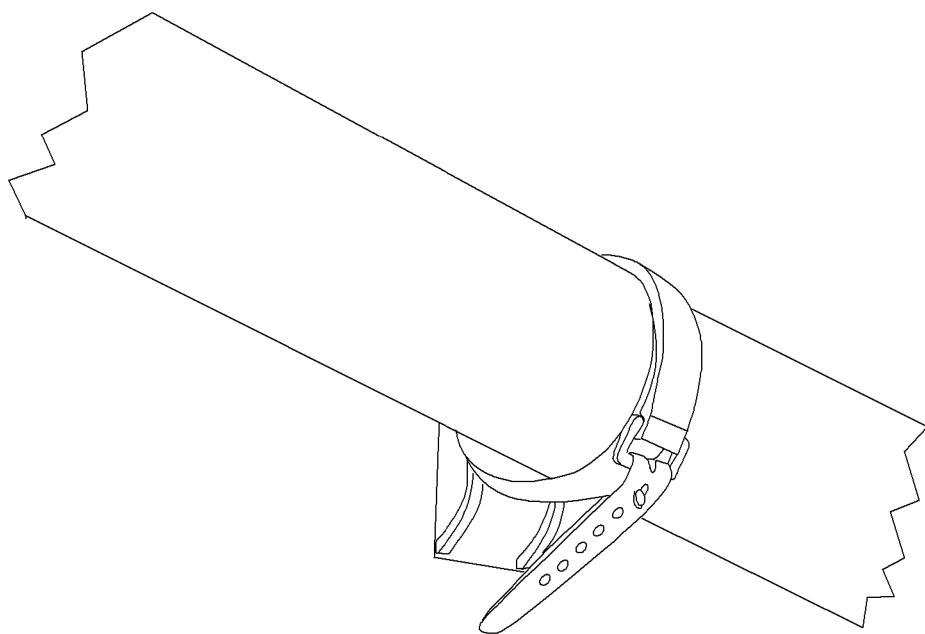
FIG. 8 shows a different view of a pipe strapped to a pipe.

FIG. 8 shows another view of the device strapped to a pipe.

Figure 9:
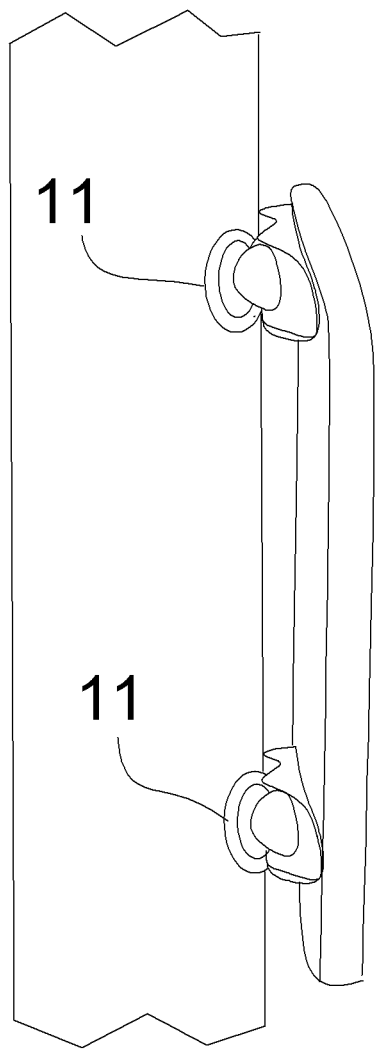
FIG. 9 shows an embodiment of the present invention using suction cups.

FIG. 9 shows an alternate embodiment of the device that uses suction cups 11 rather than a strap to attach to the pipe or other object.

Several descriptions and illustrations have been presented to aid in understanding the present invention. One with skill in the art will realize that numerous changes and variations may be made without departing from the spirit of the invention. Each of these changes and variations is within the scope of the present invention.

We claim:

1. An x-ray grid holder constructed to secure an x-ray grid to a structure comprising:
    a flat grid holder part, the grid holder part having at least one peripheral slot;
    a structure contact part constructed to be attached to a structure to be x-rayed, the structure contact part having a key sized to mate with the peripheral slot, the key having a rotating lock constructed to hold the key in the peripheral slot;
    the structure contact part having a means to attach it to the structure to be x-rayed.

2. The x-ray grid holder of claim 1 wherein the structure contact part is constructed to attach to a pipe.

3. The x-ray grid holder of claim 1 wherein the means to attach is a strap.

4. The x-ray grid holder of claim 1 wherein the means to attach is a plurality of suction cups.

5. The x-ray grid holder of claim 1 wherein the means to attach is a plurality of magnets.

6. The x-ray grid holder of claim 1 wherein the structure contact part is constructed to attach to a flat surface.

7. The x-ray grid holder of claim 1 wherein the structure to be x-rayed is a pipe.

8. The x-ray grid holder of claim 1 wherein the contact part is constructed to attach and hold the grid holder part above the surface of an object being x-rayed.

9. A method of supplying an x-ray grid holder constructed to be attached to a structure comprising:
    providing a flat grid holder part, the grid holder part having at least one peripheral slot;
    providing a structure contact part constructed to be strapped to a structure to be x-rayed, the structure contact part having a key sized to mate with the peripheral slot, the key having a lock constructed to hold the key in the peripheral slot; the structure contact part having a means to attach it to the structure to be x-rayed.

10. The method of claim 9 wherein the means to attach is a strap.

11. The method of claim 9 wherein the means to attach is a plurality of suction cups.

12. The method of claim 9 wherein the structure contact part is constructed to attach to a flat surface.

13. The method of claim 9 wherein the structure to be x-rayed is a pipe.

14. An x-ray grid holder comprising:
    a frame adapted to hold an x-ray grid, the frame having at least one elongated slot;
    a structure holding piece with an elongated protruding key, the protruding key constructed to insert into the elongated slot in the frame;
    a rotatable lock attached to said protruding key, the rotating lock constructed to secure the structure holding piece to the frame in a locked position and release the frame in an unlocked position;
    the structure holding piece having an attachment mechanism, the attachment mechanism constructed to attach the structure holding piece to an external structure to be x-rayed.

15. The x-ray grid holder of claim 14 wherein the attachment mechanism is a strap and buckle.

16. The x-ray grid holder of claim 14 wherein the attachment mechanism is a plurality of suction cups.

17. The x-ray grid holder of claim 14 wherein the structure to be x-rayed is a pipe.

18. The x-ray grid holder of claim 14 wherein the structure to be x-rayed is flat.

19. The x-ray grid holder of claim 14 wherein the rotatable lock rotates on an axle that itself protrudes from the protruding key.

20. The x-ray grid holder of claim 14 wherein the frame has a thickness and the protruding key mates with the elongated slot, the protruding key having a height equal to the thickness of the frame.

21. The x-ray grid holder of claim 20 wherein the rotating lock is itself elongated and when in the locked position, provides a bias that pulls the protruding key against the frame.

* * * * *